United States Patent [19]

Varma et al.

[11] 3,976,637
[45] Aug. 24, 1976

[54] 3,20-DIKETOPREGNENES HAVING AN 11β-ACETAL GROUP

[75] Inventors: Ravi K. Varma, Belle Mead; Christopher M. Cimarusti, Hamilton, both of N.J.

[73] Assignee: E. R. Squibb & Sons, Inc., Princeton, N.J.

[22] Filed: Sept. 8, 1975

[21] Appl. No.: 610,955

[52] U.S. Cl. .................................. 260/239.55 D
[51] Int. Cl.² ................................. C07J 17/00
[58] Field of Search .................... 260/239.55 D

[56] References Cited
UNITED STATES PATENTS
3,758,686    9/1973    Sieger et al. .............. 260/239.55 D OTHER PUBLICATIONS
Fukushima et al., J. Org. Chem., (1961), vol. 26, p. 520.

*Primary Examiner*—Elbert L. Roberts
*Attorney, Agent, or Firm*—Lawrence S. Levinson; Merle J. Smith; Donald J. Barrack

[57] ABSTRACT

3,20-Diketopregnenes having in the 11β-position a group of the formula

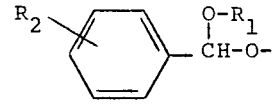

wherein $R_1$ is alkyl and $R_2$ is hydrogen, alkyl, alkoxy, or halogen, and having a cyclic 16,17-acetal or ketal group, have useful anti-inflammatory activity.

15 Claims, No Drawings

3,20-DIKETOPREGNENES HAVING AN 11β-ACETAL GROUP

BACKGROUND OF THE INVENTION

11β-Hydroxy-3,20-diketopregnenes having a cyclic 16,17-acetal or ketal group are well known and widely used anti-inflammatory agents. Exemplary of this type of steroid are halcinonide (21-chloro-9-fluoro-11β-hydroxy-2′,2′-dimethylpregn-4-eno[16α,17-d][1,3]dioxolane-3,20-dione) and triamcinolone acetonide (9-fluoro-11β,21-dihydroxy-2′,2′-dimethylpregna-1,4-dieno[16α,17-d][1,3]dioxolane-3,20-dione). The limited solubility of these pregnenes in slighty polar solvents such as ether leads to problems in formulation design.

In order to ease the problems of formulating 11β-hydroxy-3,20-diketopregnenes having a 16,17-cyclic acetal or ketal group (and in order to prepare new and useful anti-inflammatory agents), the prior art has prepared 11-keto and 11-acyloxy steroids. While these modifications do increase the solubility of the steroids, they generally result in steroids of lesser activity.

The prior art also shows that some steroids having 11-acetal groups have been prepared. For example, Fukushima et al., *J. Org. Chem.*, 26, 520 (1961) disclose the formation of 11β-(methoxymethyl)-17,20;20,21-bismethylenedioxypregn-4-ene-3-one as a by-product during the reaction of hydrocortisone with formaldehyde. Gardi et al., *J. Org. Chem.*, 27, 668 (1962) and *Tetrahedron*, 21, 179 (1965), disclose steroids having 17,21-cyclic acetal groups as substituents and in the 11-position a group of the formula $$\begin{array}{c} O-\text{alkyl} \\ | \\ R-CH-O- \end{array} \qquad I$$

wherein R is alkyl or aryl.

SUMMARY OF THE INVENTION

It is an object of this invention to provide steroids having topical and systemic anti-inflammatory activity.

It is an object of this invention to provide steroids which can be readily formulated in slightly polar solvents such as castor oil or propylene carbonate.

These, and other objects that will be readily apparent to a person of ordinary skill in the steroid art, are met by the steroids of this invention.

The steroids of this invention are those having the formula

II and the 1,2- and 6,7-dehydro derivatives thereof; pregn-4-enes and pregna-1,4-dienes are preferred. In formula II, and throughout the specification, the symbols are as defined below.

$R_1$ can be alkyl;
$R_2$ can be hydrogen, alkyl, alkoxy, or halogen;
$R_3$ can be hydrogen, acyloxy, halogen or hydroxy;
$R_4$ can be hydrogen or halogen;
$R_5$ can be hydrogen, alkyl, or aryl;
$R_6$ can be alkyl or aryl;
$R_7$ can be hydrogen, fluorine, or methyl; and
$R_8$ can be hydrogen, chlorine, or methyl.

The term alkyl, as used throughout the specification, refers to straight or branched chain alkyl groups having 1 to 8 carbon atoms. Alkyl groups having 1 to 3 carbon atoms are preferred.

The term halogen, as used throughout the specification, refers to fluorine, chlorine, bromine, and iodine.

The term acyloxy, as used throughout the specification, refers to groups wherein the acyl portion is a physiologically acceptable acid residue derived from an organic acid. Exemplary monocarboxylic acids are those having the formula Y-COOH wherein Y is alkyl, cycloalkyl of 3 to 6 carbon atoms, arylalkyl or aryl; e.g., acetic, propionic, valeric, cyclohexanecarboxylic, phenylacetic, benzoic, and toluic acids. Exemplary polycarboxylic acids are malonic, succinic, glutaric, adipic, pimelic and phthalic acids.

The term aryl, as used throughout the specification, refers to phenyl or phenyl substituted with 1 or 2 alkyl, alkoxy, or halogen groups.

The term alkoxy, as used throughout the specification, refers to a group having the formula alkyl-O-, wherein alkyl is as defined above.

DETAILED DESCRIPTION OF THE INVENTION

The steroids of this invention are physiologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a daily dosage range of 0.1 to 200 milligrams per 70 kilograms, preferably 0.3 to 100 milligrams per 70 kilograms. If administered topically, the compounds of this invention may be used in the range of 0.01 to 5.0% by weight, preferably 0.05 to 2.0% by weight, in a conventional cream or lotion.

The 3,20-diketopregnenes of formula II, wherein $R_2$ is ortho-alkyl, can be prepared by reacting an 11β-hydroxy-3,20-diketopregnene with a 1-alkoxybenzocyclobutene having the formula

III wherein $R'_2$ is hydrogen or an alkyl group having 1 to 7 carbon atoms. The reaction, which is a novel one and constitutes a part of this invention, can be run under neutral conditions in an aprotic solvent, e.g., a hydrocarbon such as benzene or toluene. While reaction conditions are not critical, the reaction will preferably be run at, or near, the reflux temperature of the solvent. This reaction is useful not only in the preparation of the steroids of this invention, but also in the preparation of other steroids containing an 11β-hydroxy group which must be protected during multi-step syntheses. The blocking group can be readily removed by acid hydrolysis.

The 3,20-diketopregnenes of formula II can be prepared by reacting an 11β-hydroxy-3,20-diketopregnene with a benzaldehyde dialkyl acetal having the formula IV
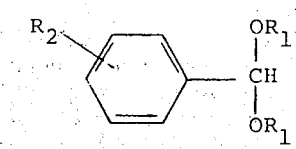

The reaction can be run in an aprotic solvent, e.g., a hydrocarbon such as benzene or toluene. The reaction is run under acid conditions (e.g., in the presence of an organic acid such as p-toluenesulfonic acid) and can be run at, or near, the reflux temperature of the solvent.

Many variations and modifications of this invention will be apparent to a person of ordinary skill in the field of steroid chemistry. If, for example, the 11β-hydroxy-3,20-diketopregnene used to prepare the steroids of this invention contains additional hydroxyl groups, they should be protected before proceeding with the above-described reactions.

The following examples are specific embodiments of this invention.

EXAMPLE 1

21-Chloro-11β-[ethoxy(2-methylphenyl)methoxy]-9-fluoro-2',2'-dimethylpregn-4-eno[16α,17-d][1,3]dioxolane-3,20-dione A suspension of 21-chloro-9-fluoro-11β-hydroxy-2',2'-dimethylpregn-4-eno[16α,17-d][1,3]dioxolane-3,20-dione (684 mg) in anhydrous toluene (17 ml) containing 1-ethoxy-1,2-dihydrobenzocyclobutene (444 mg) is refluxed in a nitrogen atmosphere. In a few minutes a homogeneous solution is obtained. After about 6 hours, the solution is cooled and then absorbed on a column of silica gel (20 g). Elution of the column with chloroform-hexane (1:4) yields unreacted 1-ethoxy-1,2-dihydrobenzocyclobutene. Further elution of the column with chloroform-hexane (1:4 and 1:1) gives the product as a foam (0.90 g). This is dissolved in the minimum amount of ether, diluted with 10 ml of hexane and maintained at a temperature of about 5°C to yield the solid (355 mg), melting point 171°–180°C. Recrystallization of this material from ethyl acetate-hexane yields the title compound (205 mg), melting point 182°–185°C.

EXAMPLE 2

9-Fluoro-11β-(methoxyphenylmethoxy)-2',2'-dimethylpregna-1,4-dieno[16α,17-d][1,3]dioxolane-3,20-dione A suspension of 9-fluoro-11β-hydroxy-2',2'-dimethylpregna-1,4-dieno[16α,17-d][1,3]dioxolane-3,20-dione (1.0 g) and benzaldehyde dimethyl acetal (2.0 g) in benzene (130 ml) containing p-toluenesulfonic acid (15 mg) is azeotropically distilled. After about 25 minutes, the solution is cooled, washed with a dilute sodium bicarbonate solution and water, dried and evaporated in vacuo to yield a solid (1.3 g). Recrystallization of this material from ethyl acetate-hexane yields the title compound (0.9 g), melting point 198°–214°C.

EXAMPLE 3

21-(Acetyloxy)-9-fluoro-11β-(methoxyphenylmethoxy)-2',2'-dimethylpregna-1,4-dieno[16α,17-d][1,3]dioxolane-3,20-dione A suspension of triamcinolone acetonide, 21-acetate (1.0 g) in benzene (150 ml) containing benzaldehyde dimethyl acetal (2.0 g) and p-toluenesulfonic acid (25 mg) is distilled removing the benzene. After about 30 minutes, the solution is cooled, washed with a dilute sodium bicarbonate solution and water, dried using magnesium sulfate and evaporated to a solid which is absorbed on a column of silica gel (40 g). Elution of the column with chloroform-hexane (1:4) removes nonsteroidal impurities. Further elution with chloroform-hexane (3:7 and 1:1) yields 0.96 mg of material which is recrystallized from ethyl acetate-hexane to yield the title compound (0.5 g), melting point 196°–198°C.

EXAMPLE 4

21-(Acetyloxy)-11β-[ethoxy(2-methylphenyl)methoxy]-9-fluoro-2',2'-dimethylpregna-1,4-dieno[16α,17-d][1,3]dioxolane-3,20-dione Triamcinolone acetonide, 21-acetate (1.0 g) is dissolved in anhydrous xylenes (37 ml) in an oil bath maintained at about 125°C in a nitrogen atmosphere. 1-Ethoxybenzocyclobutene (1.11 g) is added and after 18 hours the reaction is incomplete. The following additional amounts of 1-ethoxybenzocyclobutene are added at the indicated time intervals:

0.3ml (21 hours)
0.3ml (24 hours)
0.3ml (28 hours)
0.3ml (46 hours) and
0.3ml (48 hours).

The solution is evaporated and the residue is dissolved in chloroform and chromatographed on a silica gel column (25 mg). Elution of the column with chloroform-hexane (1:4 to 1:1) removes nonsteroidal impurities. Further elution with chloroform-hexane (4:1) and chloroform yield the desired material (0.8 g). The solid is dried to yield the title compound, melting point 105°–110°C.

EXAMPLES 5–8

Following the procedure of Example 1, but substituting the steroid listed in column I for 21-chloro-9-fluoro-11β-hydroxy-2',2'-dimethylpregn-4-eno[1-6α,17-d][1,3]dioxolane-3,20-dione and the compound listed in column II for 1-ethoxy-1,2-dihydrobenzocyclobutene, yields the steroid listed in column III.

| | Column I | Column II | Column III |
|---|---|---|---|
| 5 | 2,21-dichloro-11β-hydroxy-2',2'-dimethylpregna-1,4-dieno[16α,17-d][1,3]dioxolane-3,20-dione | 1-ethoxy-2-methyl-1,2-dihydrobenzocyclobutene | 2,21-dichloro-11β-[ethoxy(2-ethylphenyl)methoxy]-2',2'-dimethylpregna-1,4-dieno[16α,17-d][1,3]dioxolane-3,20-dione |
| 6 | 11β-hydroxy-2',2'-dimethylpregna-1,4,6-trieno[16α,17-d][1,3]dioxolane-3,20-dione | 1-propoxy-2-ethyl-1,2-dihydrobenzocyclobutene | 11β-[propoxy(2-propylphenyl)methoxy]-2',2'-dimethylpregna-1,4,6-trieno[16α,17-d][1,3]dioxolane-3,20-dione |
| 7 | 21-chloro-11β-hydroxy-2,2',2'-trimethylpregna-1,4-dieno[16α,17-d][1,3]dioxolane-3,20-dione | 1-ethoxy-1,2-dihydrobenzocyclobutene | 21-chloro-11β-[ethoxy(2-methyl)methoxyl-2,2',2'-trimethylpregna-1,4-dieno[16α,17-d][1,3]dioxolane-3,20-dione |
| 8 | 21-(benzoyloxy)-11β-hydroxy-2',2'-diphenylpregna-1,4-dieno[16α,17-d][1,3]dioxolane-3,20-dione | 1-ethoxy-1,2-dihydrobenzocyclobutene | 21-(benzoyloxy)-11β-[ethoxy(2-methylphenyl)methoxy]-2',2'-diphenylpregna-1,4-dieno[16α,17-d][1,3]dioxolane-3,20-dione |

EXAMPLES 9–11

Following the procedure of Example 2, but substituting the steroid listed in column I for 9-fluoro-11β-hydroxy-2',2'-dimethylpregna-1,4-dieno[16α,17-d][1,3]dioxolane-3,20-dione and the compound listed in column II for benzaldehyde dimethyl acetal, yields the steroid listed in column III.

| | Column I | Column II | Column III |
|---|---|---|---|
| 9 | 6α,9-difluoro-11β-hydroxy-2',2'-dimethylpregn-4-eno[16α,17-d][1,3]dioxolane-3,20-dione | 4-chlorobenzaldehyde dimethyl acetal | 6α,9-difluoro-11β-[methoxy(4-chlorophenyl)methoxy]-2',2'-dimethylpregn-4-eno[16α,17-d][1,3]dioxolane-3,20-dione |
| 10 | 9-fluoro-11β-hydroxy-2',2',6α-trimethylpregn-4-eno[16α,17-d][1,3]dioxolane-3,20-dione | 3-methoxybenzaldehyde diethyl acetal | 9-fluoro-11β[ethoxy (3-methoxyphenyl)methoxy]-2',2',6α-trimethylpregn-4-eno[16α,17-d][1,3]dioxolane-3,20-dione |
| 11 | 9-fluoro-11β-hydroxy-2',2'-dimethylpregn-4-eno[16α,17-d][1,3]dioxolane-3,20-dione | 2-methylbenzaldehyde dimethyl acetal | 9-fluoro-11β-[methoxy(2-methylphenyl)methoxy]-2',2'-dimethylpregn-4-eno-[16α,17-d][1,3]dioxolane-3,20-dione |

EXAMPLE 12

9-Fluoro-21-hydroxy-11β-(methoxyphenylmethoxy)-2',2'-dimethylpregna-1,4-dieno[16α,17-d][1,3]dioxolane-3,20-dione A suspension of 21-(acetyloxy)-9-fluoro-11β-(methoxyphenylmethoxy)-2',2'-dimethylpregna-1,4-dieno[16α,17-d][1,3]dioxolane-3,20-dione (0.7 g, prepared as described in Example 3) in 75 ml of methanol is cooled to 0°C and 7 ml of 10% potassium carbonate solution is added. After 15 minutes, 20 ml of 20% aqueous acetic acid is added followed by water, and the resulting solid is filtered and dried in vacuo to yield the title compound.

What is claimed is:

1. A steroid having the formula

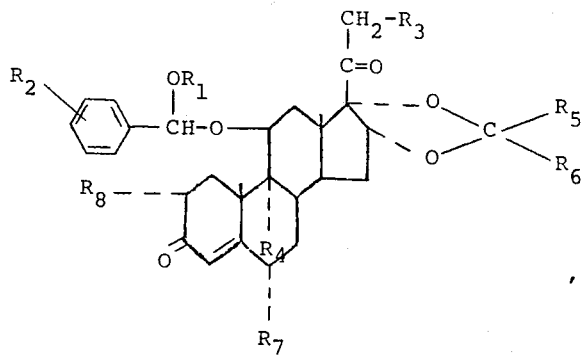

or a 1,2- or 6,7-dehydro derivative thereof, wherein $R_1$ is alkyl; $R_2$ is hydrogen, alkyl, alkoxy, or halogen; $R_3$ is hydrogen, acyloxy, halogen, or hydroxy; $R_4$ is hydrogen or halogen; $R_5$ is hydrogen, alkyl, or aryl; $R_6$ is alkyl or aryl; $R_7$ is hydrogen, fluorine, or methyl; and $R_8$ is hydrogen, chlorine, or methyl.

2. A steroid in accordance with claim 1 wherein $R_4$ is fluorine, $R_7$ is hydrogen, and $R_8$ is hydrogen.

3. A steroid in accordance with claim 2 wherein $R_5$ and $R_6$ are each methyl.

4. A steroid in accordance with claim 3 wherein $R_3$ is hydrogen.

5. A steroid in accordance with claim 3 wherein $R_3$ is acyloxy.

6. A steroid in accordance with claim 3 wherein $R_3$ is halogen.

7. A steroid in accordance with claim 3 wherein $R_3$ is hydroxy.

8. A steroid in accordance with claim 2 wherein $R_2$ is hydrogen or methyl.

9. A steroid in accordance with claim 3 wherein $R_2$ is hydrogen or methyl.

10. The steroid in accordance with claim 1 having the name 21-chloro-11β-[ethoxy(2-methylphenyl)methoxy]-9-fluoro-2',2'-dimethylpregn-4-eno[16α,17-d][1,3]dioxolane-3,20-dione.

11. The steroid in accordance with claim 1 having the name 9-fluoro-11β-(methoxyphenylmethoxy)-2',2'-dimethylpregna-1,4-dieno[16α,17-d][1,3]dioxolane-3,20-dione.

12. The steroid in accordance with claim 1 having the name 21-(acetyloxy)-9-fluoro-11β-(methoxyphenylmethoxy)-2',2'-dimethylpregna-1,4-dieno[16α,17-d][1,3]dioxolane-3,20-dione.

13. The steroid in accordance with claim 1 having the name 21-(acetyloxy)-11β-[ethoxy(2-methylphenyl)methoxy]-9-fluoro-2',2'-dimethylpregna-1,4-dieno[16α,17-d][1,3]dioxolane-3,20-dione.

14. A process for preparing a steroid having in the 11β-position a group of the formula

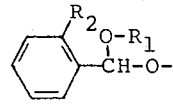

wherein $R_1$ and $R_2$ are the same or different and are each alkyl having 1 to 8 carbon atoms, which comprises reacting a 1-alkoxybenzocyclobutene having the formula

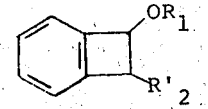

wherein $R_1$ is alkyl having 1 to 8 carbon atoms and $R_2$ is hydrogen or alkyl having 1 to 7 carbon atoms, with an 11β-hydroxy steroid under substantially neutral conditions.

15. A process in accordance with claim 14 wherein $R_2$ is methyl and $R'_2$ is hydrogen.

* * * * *